United States Patent [19]

Oda et al.

[11] Patent Number: 4,840,959
[45] Date of Patent: Jun. 20, 1989

[54] PYRIDINECARBOXAMIDE DERIVATIVES AND THEIR USE AS FUNGICIDE

[75] Inventors: Masatsugu Oda, Yokohama; Naoko Sasaki, Tokyo; Toshiro Sakaki, Yokohama; Hirofumi Tomita, Tokyo; Nobuyuki Nonaka, Yokohama, all of Japan

[73] Assignee: Mitsubishi Chemical Industries Limited, Tokyo, Japan

[21] Appl. No.: 84,173

[22] Filed: Aug. 12, 1987

[30] Foreign Application Priority Data

Aug. 12, 1986 [JP] Japan .................................. 61-188936
Oct. 21, 1986 [JP] Japan .................................. 61-250472
Apr. 13, 1987 [JP] Japan .................................. 62-90371

[51] Int. Cl.$^4$ .................. C07D 213/46; A61K 31/455
[52] U.S. Cl. ..................................... 514/355; 546/316
[58] Field of Search ........................ 546/316; 514/355

[56] References Cited

U.S. PATENT DOCUMENTS 4,001,416  1/1977  Pommer et al. ..................... 514/341
4,511,581  4/1985  Ohsumi et al. ..................... 564/166

*Primary Examiner*—Jane T. Fan
*Attorney, Agent, or Firm*—Oblon, Spivak, McClelland, Maier & Neustadt

[57] ABSTRACT

Disclosed are novel pyridinecarboxamide derivatives represented by the general formula:

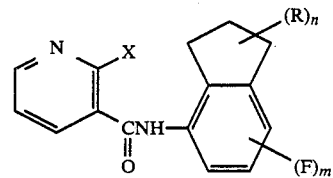

wherein X represents a halogen atom, methyl group or trifluoromethyl group, R represents a lower alkyl group or halogen atom, n represents an integer of 1 to 6, and m represents 0 or 1, and a fungicide containing such derivative as active ingredient.

10 Claims, No Drawings

PYRIDINECARBOXAMIDE DERIVATIVES AND THEIR USE AS FUNGICIDE

FIELD OF THE INVENTION

This invention relates to pyridine-3-carboxamide derivatives and to fungicide containing them as active ingredient.

BACKGROUND OF THE INVENTION

It is known that certain species of pyridinecarboxamide derivatives are fungicidally active. For instance, DT-OS No. 2,417,216 shows that a compound of the formula:

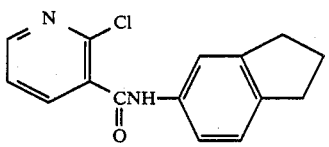

may be applicable as a fungicide, and DT-OS No. 2,611,601 describes that a compound represented by the formula:

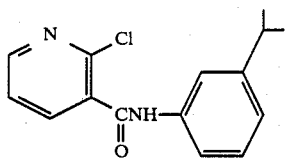

has fungicidal activity. Also, in Japanese Patent Application Laid-Open (Kokai) No. 58-140054 a compound represented by the formula:

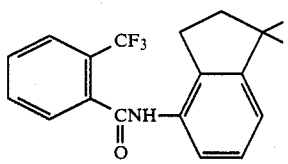

has the fungicidal activity, and PCT International Publication No. WO 86/02641 shows that a compound of the formula:

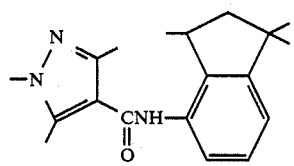

is also fungicidal. However, from biological Test Results hereinunder described, any of these compounds does not always show sufficient fungicidal activity.

Benzimidazole or thiophanate fungicides such as benomyl [methyl-1-(butylcarbamoyl)-benzimidazol-2-yl carbamate] and thiophanate methyl [1,2-bis(3-methoxycarbonyl-2-thioureido)benzene] exhibited excellent fungicidal effect against various species of pathogenic fungi causing damages on agricultural and horticultural plants, and they had been used extensively since 1970s. However, resistant strains to these fungicides have been appearing and spreading world wide, and accordingly these fungicides are practically useless at present.

Cyclic imide fungicides such as Procymidone [N-(3,5-dichlorophenyl)-1,2-dimethylcyclopropane-1,2-dicarboxyimide] have come to be used widely in place of the benzimidazole or thiophanate fungicides, since such cyclic imide fungicides were effective against the drug-resistant strains of Botrytis to benzimidazoles or thiophanates. But in recent years there have appeared resistant strains to these cyclic imide type fungicides and these fungicides were practically useless in the field.

It has been reported that N-phenyl carbamate compounds disclosed in Japanese Patent Application Laid-Open (Kokai) No. 58-126856 exhibited a high activity against both of these resistant strains. These N-phenyl carbamate compounds are, however, quite ineffective against sensitive strains to benzimidazole or thiophanate and cyclic imide fungicides, so that they are occasionally useless by alone.

The object of the present invention is to provide novel chemicals having strong fungicidal activity against both of drug-resistant and sensistive strains.

SUMMARY OF THE INVENTION

The present invention provides novel pyridine-3-carboxamide derivatives represented by the general formula I:

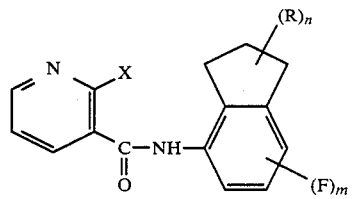

wherein X represents a halogen atom, methyl group or trifluoromethyl group; R represents a lower alkyl group or halogen atom; n represents an integer of 1 to 6; and m represents 0 or 1, and further provides fungicides containing them as active ingredient.

DETAILED DESCRIPTION OF THE INVENTION

In the aforementioned formula I, X represents halogen such as fluorine, chlorine, bromine or iodine atom, methyl group or trifluoromethyl group. R represents a straight or branched lower alkyl group having 1 to 5 carbon atoms such as methyl, ethyl, n-propyl, iso-propyl group, etc., preferably a lower alkyl group having 1 to 3 carbon atoms; or halogen such as fluorine, chlorine, bromine or iodine atom. The symbol n represents an integer of 1 to 6, and when n is an integer of 2 to 6, the plural substituents R may be indentical or different. Preferably n is an integer of 1 to 5.

Typical examples of the compounds according to the invention represented by the formula I are shown in Table 1 below, but the compounds of this invention are on no account limited to those examples.

TABLE 1

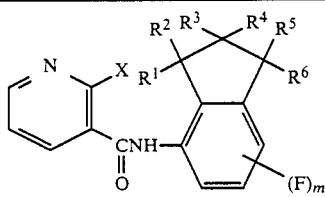

| X | R¹ | R² | R³ | R⁴ | R⁵ | R⁶ | m | Position of F |
|---|---|---|---|---|---|---|---|---|
| F | CH₃ | H | CH₃ | H | H | H | 0 | — |
| F | H | H | H | H | CH₃ | CH₃ | 0 | — |
| F | CH₃ | H | H | H | CH₃ | CH₃ | 0 | — |
| F | CH₃ | H | CH₃ | H | C₂H₅ | H | 0 | — |
| F | H | H | H | H | CH₃ | CH₃ | 0 | — |
| F | CH₃ | CH₃ | H | H | H | H | 0 | — |
| F | iso-C₃H₇ | H | H | C₂H₅ | F | H | 0 | — |
| Cl | H | H | H | H | H | iso-C₃H₇ | 0 | — |
| Cl | CH₃ | H | C₂H₅ | H | CH₃ | H | 0 | — |
| Cl | H | H | H | H | CH₃ | CH₃ | 0 | — |
| Cl | H | H | H | H | C₂H₅ | H | 0 | — |
| Cl | CH₃ | CH₃ | H | H | H | H | 0 | — |
| Cl | CH₃ | H | H | H | CH₃ | H | 0 | — |
| Cl | H | H | iso-C₃H₇ | H | C₂H₅ | H | 0 | — |
| Cl | Cl | H | CH₃ | H | Cl | H | 0 | — |
| Cl | Cl | H | CH₃ | C₂H₅ | Cl | H | 0 | — |
| Cl | CH₃ | CH₃ | H | H | CH₃ | CH₃ | 0 | — |
| Cl | n-C₃H₇ | H | H | H | n-C₃H₇ | H | 0 | — |
| Cl | H | C₂H₅ | H | CH₃ | H | Br | 0 | — |
| Cl | CH₃ | CH₃ | H | H | H | CH₃ | 0 | — |
| Cl | CH₃ | H | H | H | CH₃ | CH₃ | 1 | 5 |
| Cl | H | H | H | H | CH₃ | CH₃ | 1 | 6 |
| Cl | H | CH₃ | H | H | CH₃ | CH₃ | 1 | 7 |
| Cl | CH₃ | H | H | H₆ | CH₃ | CH₃ | 0 | — |
| Br | C₂H₅ | H | H | H | n-C₃H₇ | H | 0 | — |
| Br | H | H | H | H | C₂H₅ | C₂H₅ | 0 | — |
| Br | H | H | n-C₃H₇ | H | H | CH₃ | 0 | — |
| Br | C₂H₅ | H | H | n-C₃H₇ | H | H | 0 | — |
| Br | H | H | H | H | C₂H₅ | C₂H₅ | 0 | — |
| Br | CH₃ | Cl | H | H | H | H | 0 | — |
| Br | H | iso-C₃H₇ | H | H | iso-C₃H₇ | H | 0 | — |
| Br | CH₃ | CH₃ | H | H | H | H | 0 | — |
| I | CH₃ | H | CH₃ | H | CH₃ | CH₃ | 0 | — |
| CF₃ | CH₃ | H | H | H | CH₃ | CH₃ | 0 | — |
| CH₃ | CH₃ | H | H | H | CH₃ | CH₃ | 0 | — |
| CF₃ | H | H | H | H | CH₃ | CH₃ | 0 | — |

The compounds of this invention are all novel and may be synthesized, for instance, according to the following reaction route:

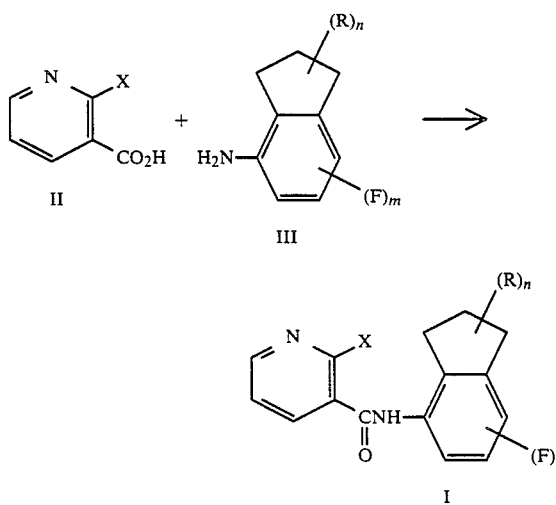

wherein X, R, n and m are defined as above.

The above reaction is accomplished by reacting a pyridine-3-carboxylic acid of the formula II or reactive derivative thereof and an aminoindane derivative of the formula III in the presence or absence of a solvent inert to the reaction.

The amount of pyridine-3-carboxylic acid or its derivative of the formula II used in the above reaction is in the range of 0.5 to 1.5 equivalents, preferably, 0.9 to 1.1 equivalents to the aminoindane derivative of the formula III. This reaction may proceed in a temperature range from $-70°$ C. to a boiling point of the solvent used, preferably, from $-40°$ C. to the boiling point of the solvent.

Examples of the pyridine-3-carboxylic acid or its derivative represented by the formula II include corresponding carboxylic acids, acid anhydrides, acid halides such as acid chloride, and carboxylic acid esters.

The solvents usable in the above reaction include aromatic hydrocarbons such as benzene, toluene, etc., halogenated hydrocarbons such as carbon tetrachloride, chloroform, etc., aromatic halogenated hydrocarbons such as chlorobenzene, ethers such as diethyl ether, tetrahydrofurane, dioxane, etc., esters such as ethyl acetate, and polar solvents such as dimethyl sulfoxide, dimethylformamide, water, etc.

For allowing smooth facilitation of the reaction, there can be used a suitable reaction assisting agent selected depending on the type of pyridine-3-carboxylic acid or its derivatives of the formula II.

As the reaction assisting agent dehydrating agents such as ethoxyacetylene, dicyclohexylcarbodiimide and phosphorus pentoxide can be used in case of carboxylic acids; tertiary amines such as N-methylmorpholine and trietylamine or aromatic bases such as pyridine, picoline and N,N-diethylaniline can be used in case of acid anhydrides; tertiary amines such as triethylamine, aromatic bases such as pyridine and picoline, alkaline metal hydroxides such as sodium hydroxide and potassium hydroxide, alkali metal hydrides such as sodium hydride, or alkali metal alcoholates such as sodium ethylate can be used in case of acid halides; and alkali metal alcoholates such as sodium ethylate can be used in case of carboxylic acid esters.

Such reaction assisting agent may be used usually by 0.01 to 5.0 equivalents, preferably by 0.9 to 1.1 equivalents to the aminoindane derivatives of the formula III.

Alternatively the compounds of the invention may as well be prepared according to the following reaction route:

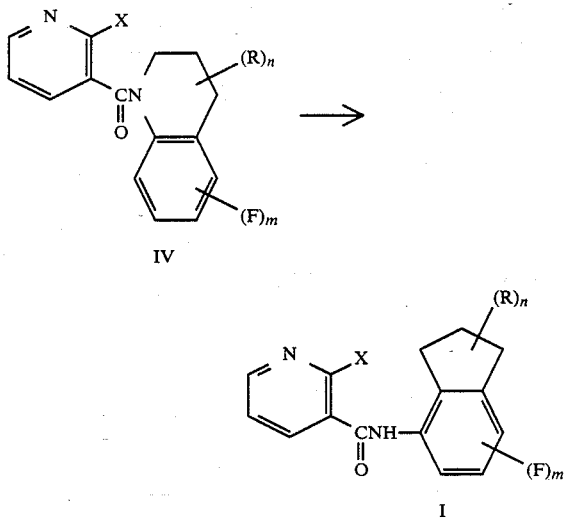

wherein X, R, n and m represent the same as defined in the formula I above.

The above reaction is accomplished by internal rearrangement of acyltetrahydroquinoline derivative of the formula IV in the presence of an acid catalyst at a temperature of −40° C. to 200° C., preferably 0° C. to 150° C.

The acid catalyst usable in this reaction include sulfuric acid, phosphoric acid, polyphosphoric acid, Lewis acid and the like ranging from 0.001 equivalents to a large excess to the amount of the acyltetrahydroquinoline derivative.

Among the compounds of this invention, 2-fluoropyridine derivatives of which symbol X in the formula I, II or IV is fluorine atom can be prepared from 2-chloropyridine derivatives of the formula I, II or IV by an ordinary chlorine/fluorine exchange reaction. In this case, an ordinary fluorinating agent such as potassium fluoride, cesium fluoride or the like may be used as reacting agents.

Compounds prepared in the manner described above are all novel and have excellent fungicidal activity.

Especially, these compounds exhibit a marvellous controlling action against the fungi pathogenic to various species of plants and are quite useful as the fungicide for agricultural and horticultural use. For instance, the compounds show a strong fungicidal effect against *Rhizoctonia solani* on rice, *Puccinia recondita, Typhula incarnate* and *T. ishikariensis* on wheat, *Rhizoctonia solani* on lawn grass and pasture, *Sclerotinia sclerotiorum* and *Botrytis cinerea* on various kinds of crops. It is particularly noticeable that the compounds of the present invention show an extremely high activity against the sensitive and resistant strains of *Botrytis cinerea* to the fungicide of benzimidasole, thiophanate and cyclic imides. These compounds, therefore, are useful as the agricultural and horticultural fungicide.

Further, the compounds of this invention cause almost no phytotoxicity to the plants and are also low in toxicity to human beings and livestock and fishes as well, so that they are very useful for the prevention of plant fungal diseases.

The fungicides according to the invention may be composed of only the compound of the formula I, but it is preferred to use them in a form of emulsifiable concentrate, wettable powder, dust or the like by adding suitable adjuvant(s) in a known way for making the dispersion of active ingredient more effective in the actual application.

The solvents which can be used as an adjuvant for the fungicide of this invention include, for example, water, alcohols (methyl alcohol, ethyl alcohol, ehylene glycol, etc.), ketones (acetone, methyl ethyl ketone, cyclohexane, etc.), ethers (ethyl ether, dioxane, cellosolves, etc.), aliphatic hydrocarbons (Kerosene, paraffin oil, fuel oil, etc.), aromatic hydrocarbons (benzene, toluene, xylene, solvent naphtha, methyl naphthalene, etc.), halogenated hydrocarbons (dichloroethane, trichlorobenzene, carbon tetrachloride, etc.), acid amides (dimethylformamide, etc.), esters (ethyl acetate, butyl acetate, glycerin esters of fatty acids, etc.), nitriles (acetonitrile, etc.) and the like. These solvents may be used either singly or as a mixture.

As filler, it is recommended to use mineral powders, e.g., pulverized clays such as kaolin, bentonite, etc., talc, pyrophyllite, oxides such as diatomaceous earth, white carbon, etc., and powders of plant such as soybean powder, CMC, etc., either singly or as a mixture.

It is also possible to use a surfactant as a spreading agent, dispersing agent, emulsifying agent or penetrating agent. The surfactant usable for this purpose includes nonionic surfactants (polyoxyethylene alkylaryl ether, polyoxyethylene sorbitan monolaurate, etc.), cationic surfactants (alkyldimethyl benzylammonium chloride, alkylpyridinium chloride, etc.), anionic surfactants (alkylbenzene sulfonate, lignin sulfonate, higher alcohol sulfate, etc.) and amphoteric surfactants (alkyldimethylbetaine, dodecylaminoethylglycine, etc.).

These surfactants may be used either singly or in combination according to the purpose of use of the fungicide of this invention.

In practical application of the fungicide in the formulation of emulsifiable concentrate, 10 to 50 parts of the compound of this invention, 10 to 80 parts of solvent and 3 to 20 parts of surfactant(s) are mixed in a suitable ratio to prepare the formulation, and in use, this formulation may be diluted with water to a desired concentration and applied by a suitable method such as spraying.

In case of using the fungicide in the formulation of wettable powder, 5 to 80 parts of the compound of this invention, 10 to 90 parts of filler(s) and 1 to 20 parts of surfactant are mixed in a suitable ratio and the mixture may be properly diluted with water (or the like) as in the case of emulsifiable concentrate.

In case of using the fungicide in the formulation of dust, usually 1 to 5 parts of the compound of this invention may be uniformly mixed with 95 to 99 parts of pulverized bulk filler(s) such as kaoline, bentonite, talc, etc.

The fungicide of this invention may be mixed with other pesticidal chemicals such as another fungicide, insecticide, miticide, etc., which won't affect the fungicidal effect of the active ingredient according to the invention.

As for the way of application of the fungicide of this invention, it can be effectively applied either by spraying or spreading to stalks and leaves of plants or by application to water surface. In the case of spraying to stalks and leaves of plants, usually the emulsifiable concentrate or wettable powder is diluted with water to a concentration of 10 to 1,000 ppm and applied at a ratio of 10 to 500 liters per 10 ares.

The present invention will hereinafter be described in further detail by referring to Examples thereof, but it is to be understood that those Examples are merely intended to be illustrative and not limitative of the scope of the invention.

In the following descriptions of Examples, all "parts" are by weight unless otherwise noted. All structures of the compounds according to this invention prepared in Synthesis Examples shown below were confirmed by elementary analysis, IR spectrum and NMR spectrum.

SYNTHESIS EXAMPLE 1

Synthesis of 2-chloro-N-(1,1-dimethylindan-4-yl)-pyridine-3-carboxamide

To a solution of 200 mg (1.2 mmol) of 4-amino-1,1-dimethylindane and 0.15 g (1.9 mmol) of pyridine in 15 ml of ethyl acetate was added 0.24 g (1.4 mmol) of 2-chloronicotinic acid chloride under ice cooling, and the mixture was stirred at room temperature for one hour. The reaction mixture was poured into ice water and extracted with ethyl acetate. The extract was washed with water, dried over Glauber's salt and then concentrated under reduced pressure. The white residue was recrystallized with hexane to obtain 300 mg of white crystals (Compound No. 1 shown in Table 2). The yield was 80.4%.

SYNTHESIS EXAMPLE 2

Synthesis of 2-chloro-N-(1-chloro-3-methylindan-4-yl)-pyridine-3-carboxamide

To a solution of 1 g (5.5 mmol) of 4-amino-1-chloro-3-methylindane and 0.7 g (6.9 mmol) of triethylamine in 15 ml of tetrahydrofuran was added 1.1 g (6.2 mmol) of 2-chloronicotinic acid chloride under ice cooling, and the mixture was stirred at room temperature for one hour. The reaction mixture was poured into ice water and extracted with ethyl acetate. The extract was washed with water, dried over Glauber's salt and then concentrated under reduced pressure. The residue was separated and purified by silica gel chromatography (eluent: n-hexane/ethyl acetate=2/1) to obtain 1.3 g of white crystals (Compound No. 6 shown in Table 2) in a yield of 75%.

SYNTHESIS EXAMPLE 3

Synthesis of 2-fluoro-N-(1,1,3-trimethylindan-4-yl)pyridine-3-carboxamide

To a solution of 2.6 g (14.8 mmol) of 2-chloronicotinic acid chloride in 15 ml of sulforan was added 2.6 g (46.4 mmol) of potassium fluoride, and the mixture was stirred under heating at 155° C. for 6 hours. After cooling, precipitated crystals were filtered out. The filtrate was added dropwise to a solution of 2 g (11.4 mmol) of 4-amino-1,1,3-trimethylindane and 1.6 g (15.8 mmol) of triethylamine in 10 ml of toluene under ice cooling, and the mixture was stirred at room temperature for 2 hours. The reaction solution was then added with 30 ml of toluene, washed with water, dried over Glauber's salt and concentrated under reduced pressure. The residue was purified by silica gel chromatography (eluent: n-hexane/ethyl acetate=4/1) to obtain 1.6 g of oil (Compound No. 9 shown in Table 2) in a yield of 47%.

SYNTHESIS EXAMPLE 4

Compounds of this invention shown in Table 2 were prepared according to the procedures of Synthesis Examples 1 to 3.

TABLE 2

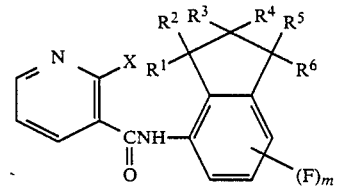

| compound No. | X | R¹ | R² | R³ | R⁴ | R⁵ | R⁶ | m | Position of F | Properties |
|---|---|---|---|---|---|---|---|---|---|---|
| 1 | Cl | H | H | H | H | CH₃ | CH₃ | 0 | — | mp. 113–114° C. |
| 2 | Cl | CH₃ | H | H | H | CH₃ | CH₃ | 0 | — | mp. 132–133° C. |
| 3 | Cl | H | H | H | H | CH₃ | H | 0 | — | mp. 118–119° C. |
| 4 | Cl | H | H | CH₃ | H | H | H | 0 | — | mp. 132–134° C. |
| 5 | Cl | CH₃ | H | H | H | H | H | 0 | — | mp. 152–153° C. |

TABLE 2-continued

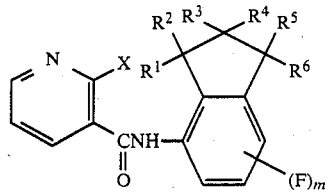

| compound No. | X | $R^1$ | $R^2$ | $R^3$ | $R^4$ | $R^5$ | $R^6$ | m | Position of F | Properties |
|---|---|---|---|---|---|---|---|---|---|---|
| 6 | Cl | H | CH$_3$ | H | H | H | Cl | 0 | — | mp. 169-180° C. |
| 7 | Cl | CH$_3$ | H | H | H | CH$_3$ | CH$_3$ | 1 | 5 | mp. 159-160° C. |
| 8 | Cl | CH$_3$ | H | H | H | CH$_3$ | CH$_3$ | 1 | 7 | mp. 127-128° C. |
| 9 | F | CH$_3$ | H | H | H | CH$_3$ | CH$_3$ | 0 | — | $n_D^{25.0}$ 1.5685 |

SYNTHESIS EXAMPLE 5

Synthesis of 2-trifluoromethyl-N-(1,1,3-trimethylindan-4-yl)-pyridine-3-carboxamide To a solution of 0.73 g (4.2 mmol) of 4-amino-1,1,3-trimethylindane and 1.5 g (14.9 mmol) of triethylamine in 60 ml of ethyl acetate was added 1.10 g (5.2 mmol) of 2-trifluoronicotinic acid chloride under ice cooling, and the mixture was stirred at room temperature for 3 hours. The reaction solution was washed with water, dried over Glauber's salt and then concentrated under reduced pressure. The residue was recrystallized with hexane/ethyl acetate to obtain 1.12 g of white crystals (Compound No. 10 shown in Table 3) in a yield of 80.6%.

SYNTHESIS EXAMPLE 6

Compound Nos. 11-13 shown in Table 3 were prepared according to the procedures of Synthesis Example 5.

TABLE 3

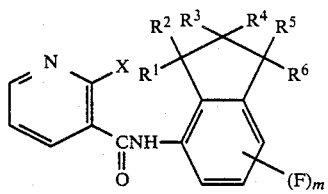

| compound No. | X | $R^1$ | $R^2$ | $R^3$ | $R^4$ | $R^5$ | $R^6$ | m | Position of F | Properties |
|---|---|---|---|---|---|---|---|---|---|---|
| 10 | CF$_3$ | CH$_3$ | H | H | H | CH$_3$ | CH$_3$ | 0 | — | mp. 172-173° C. |
| 11 | CH$_3$ | CH$_3$ | H | H | H | CH$_3$ | CH$_3$ | 0 | — | mp. 112-113° C. |
| 12 | CF$_3$ | H | H | H | H | CH$_3$ | CH$_3$ | 0 | — | mp. 149-152° C. |
| 13 | CH$_3$ | H | H | H | H | CH$_3$ | CH$_3$ | 1 | 7 | mp. 104-107° C. |

FORMULATION EXAMPLE 1

20 parts of Compound No. 1, 75 parts of diatomaceous earth, 5 parts of surfactant mainly composed of alkylbenzenesulfonate were uniformly pulverized and mixed to obtain a formulation of wettable powder.

FORMULATION EXAMPLE 2

40 parts of Compound No. 10, 10 parts of white carbon, 47 parts of diatomaceous earth and 3 parts of surfactant mainly composed of SORPOL 5039 (trade mark of polyoxyethylene alkylarylether sulfonate; manufactured and sold by Toho Chemical Industries Co., Ltd.) were uniformly pulverized and mixed to obtain a formulation of wettable powder.

FORMULATION EXAMPLE 3

30 parts of Compound No. 2, 15 parts of SORPOL 3005X (trade mark of a mixture of nonionic and anionic surfactants; manufactured and sold by Toho Chemical Industries Co., Ltd.), 25 parts of i-propylbenzene and 30 parts of N-methylpyrolidone were mixed and dissolved to obtain a formulation of emulsifiable concentrate.

FORMULATION EXAMPLE 4

2 parts of Compound No. 1 and 98 parts of N,N-Kaolin clay (available from Tsuchiya Kaolin Co., Ltd.) were mixed and pulverized to obtain a formulation of dust.

Test Examples in vivo are shown below to clarify the utility of the compounds of this invention as the fungicide.

The compounds of this invention used in the tests are indicated by the compound number shown in Tables 2 and 3, and the compounds used as comparison in the tests are indicated by compound symbol shown in Table 4 below.

TABLE 4

| Compound symbol | Chemical Structure | Remarks |
|---|---|---|
| A | (2-chloropyridin-3-yl)carboxamide of 1-methyl-1-(phenyl)ethylamine | Compound disclosed in DT-OS No. 2,611,601 |
| B | 3,4-diethoxyphenyl isobutyramide | Compound disclosed in Japanese Pat. Appln. Kokai No. 126856/83 |
| C | N-(3,5-dichlorophenyl)-1,2-dimethylcyclopropane-1,2-dicarboximide | Commercially available fungicide "Procymidone" |
| D | (2-chloropyridin-3-yl)carboxamide of 2,3-dihydro-1H-inden-5-amine | Compound disclosed in DT-OS No. 2,417,216 |
| E | 2-(trifluoromethyl)-N-(1,1,3,3-tetramethyl-2,3-dihydro-1H-inden-4-yl)benzamide | Compound disclosed in Japanese Pat. Appln. Kokai No. 140054/83 |
| F | 1,3-dimethyl-5-methyl-N-(1,1,3,3-tetramethyl-2,3-dihydro-1H-inden-4-yl)-1H-pyrazole-4-carboxamide | Compound disclosed in PCT Internat. Pub. No. WO 86/02641 |

TEST EXAMPLE 1

Preventive test against sensitive strain of *Botrytis cinerea* to benzimidazoles on cucumber A wettable powder prepared according to Formulation Example 1 and diluted with water to a predetermined concentration was sprayed, at a rate of 10 ml per pot, to stalks and leaves of cotyledon-stage cucumber (species: Suyo) cultured in pots of 6 cm in diameter. After air drying the applied chemical liquid, chemicals-sensitive strain of *Botrytis cinerea* which had been shaking-cultured in a liquid medium of yeast glucose was inoculated by spraying followed by kept in a humid chamber of 23° C. for 4 days. Thereafter, the state of morbidity was examined and evaluated in the following way.

A ratio of morbid area to total surface area of each examined leaf was determined and classified into four indieces of 0, 1, 3 and 5 as shown in the following table, and the degree of morbidity was calculated from the following formula by counting the number of leaves ($n_0$, $n_1$, $n_3$, $n_5$) corresponding to each morbidity index (n being the total number of leaves examined).

| Morbidity Index | Ratio of Morbid Area |
|---|---|
| 0 | Leaf had no sign of morbidity. |
| 1 | Leaf was morbid up to about ¼ of its total surface area. |
| 3 | Leaf was morbid through ¼ to ½ of its total surface area. |
| 5 | Leaf was morbid more than ½ of its total surface area. |

$$\text{Degree of morbidity} = \frac{0 \times n_0 + 1 \times n_1 + 3 \times n_3 + 5 \times n_5}{n}$$

Prevention value was calculated from the following formula:

Prevention value (%) =

-continued $$\frac{\text{(degree of morbidity in untreated plant)} - \text{(degree of morbidity in treated plant)}}{\text{(degree of morbidity in untreated plant)}} \times 100$$

"Treated plant" is previously sprayed with fungicide. "Untreated plant" is sprayed with no fungicide. The results are shown in Table 5.

TABLE 5

| Test Compound | Concentration of active ingredient (ppm) | Prevention value (%) |
|---|---|---|
| 1 | 200 | 100 |
| 2 | 200 | 100 |
| 5 | 200 | 100 |
| 6 | 200 | 100 |
| 7 | 200 | 100 |
| 8 | 200 | 100 |
| 10 | 200 | 100 |
| 11 | 200 | 100 |
| A | 200 | 0 |
|   | 500 | 0 |
| B | 200 | 0 |
|   | 500 | 0 |
| D | 200 | 0 |
|   | 500 | 0 |
| E | 200 | 0 |
|   | 500 | 0 |
| F | 200 | 0 |
|   | 500 | 0 |

TEST EXAMPLE 2

Preventive test against resistant strain of *Botrytis cinerea* to benzimidazoles on cucumber A wettable composition prepared according to Preparation Example 1 and diluted with water to a predetermined concentration was applied, at a rate of 10 ml per pot, to stalks and leaves of cotyledon-stage cucumbers (species: Suyo) cultured in pots of 6 cm in diameter. After air drying the chemical liquid, chemicals-resistant strain of *Botrytis cinerea* which had been shaking-cultured in a liquid medium of yeast glucose was inoculated by spraying. After keeping the inoculated cucumbers in a humid chamber of 23° C. for 4 days, the state of morbidity was examined and prevention value was calculated in the same way as in Test Example 1. The results are shown in Table 6.

TABLE 6

| Test Compound | Concentration of active ingredient (ppm) | Prevention value (%) |
|---|---|---|
| 1 | 200 | 100 |
| 2 | 200 | 100 |
| 5 | 200 | 100 |
| 6 | 200 | 100 |
| 7 | 200 | 100 |
| 8 | 200 | 100 |
| 10 | 200 | 100 |
| 11 | 200 | 100 |
| A | 200 | 0 |
|   | 500 | 0 |
| C | 200 | 0 |
|   | 500 | 0 |
| D | 200 | 0 |
|   | 500 | 0 |
| E | 200 | 0 |
|   | 500 | 0 |
| F | 200 | 0 |
|   | 500 | 0 |

TEST EXAMPLE 3

Preventive test against Rhizoctonia sp. on rice

A wettable composition prepared according to Preparation Example 1 and diluted with water to a predetermined concentration was applied, at a rate of 10 ml per pot, to stalks and leaves of 3 to 4 leaf stage of rice (species: Nihonbare) cultured in pots of 6 cm in diameter. After air drying the chemical liquid, a suspension of *Rhizoctonia solani* cultured in a YG medium was inoculated by spraying. After keeping the inoculated rice in a humid chamber of 29° C. for 40 hours and then further leaving them in a glass house for 3 days, the degree of morbidity was measured by observing spots appearing on the leaves and the prevention value was calculated from the following formula:

Prevention value (%) =

$$\frac{\text{(morbidity index per leaf in untreated plant)} - \text{(morbidity index per leaf in treated plant)}}{\text{(morbidity index per leaf in untreated plant)}} \times 100$$

The results are shown in Table 7.

TABLE 7

| Test Compound | Concentration of active ingredient (ppm) | Prevention value (%) |
|---|---|---|
| 1 | 200 | 100 |
| 2 | 200 | 100 |
| 3 | 200 | 100 |
| 6 | 200 | 100 |
| 10 | 200 | 100 |
| 11 | 200 | 100 |
| 12 | 200 | 100 |
| 13 | 200 | 100 |

TEST EXAMPLE 4

Preventive test against *Puccinia recondita* on wheat

A wettable composition prepared according to Preparation Example 1 and diluted with water to a predetermined concentration was applied, at a rate of 10 ml per pot, to stalks and leaves of 1 to 2 leaf stage of wheat (species: Norin #61) cultured in pots of 6 cm in diameter. After air drying the chemical liquid, a suspension of spores obtained by grinding wheat affected by *Puccinia recondita* was inoculated by spraying, and the inoculated wheat were kept in a humid chamber of 22° C. for 15 hours and then left in a glass house for 7 days.

The evaluation was made by determining a ratio of morbid area to total surface area of each leaf, and prevention value was calculated from the following formula:

Prevention value (%) =

$$\frac{\text{(average ratio of morbid area in untreated plant)} - \text{(average ratio of morbid area in treated plant)}}{\text{(average ratio of morbid area in untreated plant)}} \times 100$$

The results are shown in Table 8.

TABLE 7

| Test Compound | Concentration of active ingredient (ppm) | Prevention value (%) |
|---|---|---|
| 1 | 200 | 100 |
| 2 | 200 | 100 |
| 3 | 200 | 100 |
| 6 | 200 | 100 |

TABLE 7-continued

| Test Compound | Concentration of active ingredient (ppm) | Prevention value (%) |
| --- | --- | --- |
| 10 | 200 | 100 |
| 11 | 200 | 100 |
| 12 | 200 | 100 |
| 13 | 200 | 100 |

What is claimed is:

1. A pyridinecarboxamide derivative having the formula:

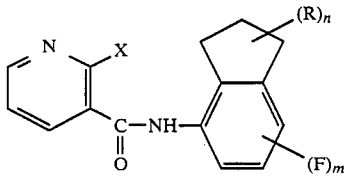

wherein X represents a halogen atom, methyl group or trifluoromethyl group, R represents a lower alkyl group or halogen atom, n represents an integer of 1 to 6, and m represents 0 or 1.

2. The pyridinecarboxamide derivative of claim 1, wherein R represents a straight or branched alkyl group having 1 to 5 carbon atoms.

3. The pyridincarboxamide derivative of claim 2, wherein R is selected from the group consisting of methyl, ethyl, n-propyl and isopropyl groups.

4. The pyridinecarboxamide derivative of claim 1, wherein R is a fluorine, chlorine, bromine or iodine atom.

5. The pyridinecarboxamide derivative of claim 1, wherein when n is an integer of 2 to 6, the plural substituents R are identical to or different from each other.

6. The pyridinecarboxamide derivative of claim 1, wherein n is an integer of 1 to 5.

7. A fungicide composition containing as an active ingredient a pyridinecarboxamide derivative having the formula:

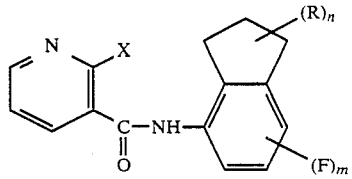

wherein X represents a halogen atom, methyl group or trifluoromethyl group, R represents a lower alkyl group or halogen atom, n represents an integer of 1 to 6, and m represents 0 or 1; and a suitable adjuvant.

8. The fungicide composition of claim 7, which is in the form of an emulsifiable concentrate, which comprises 10 to 50 parts of said pyridine carboxamide derivative, 10 to 80 parts of solvent, and 3 to 20 parts of surfactant.

9. The fungicide composition of claim 7, which is in the form of a wettable powder, which comprises 5 to 80 parts of said pyridinecarboxamide derivative, 10 to 90 parts of filler and 1 to 20 parts of surfactant.

10. The fungicide composition of claim 7, which is in the form of a dust, which comprises 1 to 5 parts of said pyridinecarboxamide derivative, and 95 to 99 parts of pulverized bulk filler.

* * * * *